United States Patent
Arth et al.

(10) Patent No.: US 6,461,636 B1
(45) Date of Patent: Oct. 8, 2002

(54) TRANSDERMAL THERAPEUTIC SYSTEM CONTAINING PERGOLIDE

(75) Inventors: Christoph Arth, Dusseldorf (DE); Andreas Kollmeyer-Seeger, Langenfeld (DE); Stephan Rimpler, Hilden (DE); Hans-Michael Wolff, Monheim (DE)

(73) Assignee: Schwarz Pharma AG, Monheim (DE)

( * ) Notice: Subject to any disclaimer, the term of this patent is extended or adjusted under 35 U.S.C. 154(b) by 0 days.

(21) Appl. No.: 09/673,069

(22) PCT Filed: May 12, 1999

(86) PCT No.: PCT/EP99/03278

§ 371 (c)(1),
(2), (4) Date: Oct. 10, 2000

(87) PCT Pub. No.: WO99/59558

PCT Pub. Date: Nov. 25, 1999

(30) Foreign Application Priority Data

May 15, 1998 (DE) .......................... 198 21 788

(51) Int. Cl.[7] .................. A61F 13/00; A61F 13/02; A61L 15/16; A61K 9/70; A01N 25/00
(52) U.S. Cl. .............. 424/449; 424/443; 424/448; 514/946; 514/947
(58) Field of Search ................ 424/448, 449, 424/443; 514/946, 947

(56) References Cited

U.S. PATENT DOCUMENTS 5,730,999 A * 3/1998 Lehmann et al. .......... 424/443

FOREIGN PATENT DOCUMENTS

| CA | 2259353 | * 8/1998 | .......... A61K/31/48 |
| DE | 43 10 012 | 9/1994 | .......... A61L/15/58 |
| DE | 196 26 621 | 1/1998 | .......... A61K/31/48 |
| WO | 96/40139 | * 12/1996 | .......... A61K/31/48 |
| WO | 99/01116 | 1/1999 | .......... A61K/9/70 |
| ZA | 985864 | 3/1998 | |

* cited by examiner

*Primary Examiner*—Thurman K. Page
*Assistant Examiner*—Humera N. Sheikh
(74) *Attorney, Agent, or Firm*—Marshall, Gerstein & Borun

(57) ABSTRACT

The invention relates to a transdermal therapeutic system (TTS) for the transcutaneous administration of pergolide over several days and to a method for its manufacture without using solvents. The TTS contains a matrix mass, containing pergolide and taking the form of a layer, which contains a (meth)acrylate copolymer containing ammonio groups or a mixture of a (meth)acrylate copolymer containing amino groups and a (meth)acrylate polymer containing carboxyl groups, 10–50% by weight propylene glycol and up to 5% by weight pergolide.

8 Claims, 1 Drawing Sheet

TRANSDERMAL THERAPEUTIC SYSTEM CONTAINING PERGOLIDE

This application is a 371 of PCT/EP 99/03278 filed May 12, 1999

DESCRIPTION

The present invention relates to a transdermal therapeutic system (TTS) for the transcutaneous administration of pergolide over several days and to a method for its manufacture without using solvents.

The bioavailability of orally administered active substances is often unsatisfactory. Hepatic metabolism of many active substances can lead on first passage through the liver to undesirable concentration ratios, toxic by-products and to reduced effect or even to loss of effect. Transdermal administration of active substances has various advantages over oral administration. The delivery of active substances can be better controlled over a longer period of time, as a result of which high fluctuations in blood levels are avoided. In addition, the required therapeutically effective dose can usually be significantly reduced. Also a plaster is often preferred by the patient to tablets, which have to be taken once or several times daily.

In the past, consideration has been given to overcoming the above disadvantages of non-transdermal administration of active substances by means of a multitude of transdermal therapeutic systems (TTSs) with different structures for different active substances treating different diseases.

The technical documents specified below therefore describe, in respect of a great variety of systemically or topically reacting active substances, their parenteral administration either on the basis of dose-controlled or generally releasing systems. By way of example, these are: U.S. Pat. Nos. 3,598,122; 3,598,123; 3,731,683; 3,797,494; 4,031,894; 4,201,211; 4,286,592; 4,314,557; 4,379,454; 4,435,180; 4,559,222; 4,568,343; 4,573,995; 4,588,580; 4,645,502; 4,702,282; 4,788,062; 4,816,258; 4,849,226; 4,908,027; 4,943,435 and 5,004,610.

In the late sixties of this century, it was originally theoretically presumed that any active substance with a short half-life but high efficacy and good skin-penetrating ability was suitable for reliable and effective administration by means of a TTS. However, these initial expectations with regard to the possibilities for the transdermal administration of active substances by means of TTSs were not fulfilled. The reasons for this were mainly that the skin is, by its very nature, endowed with an immense variety of properties to maintain its function as an intact barrier against penetration into the body of non-endogenous substances. (See in this connection: Transdermal Drug Delivery: Problems and Possibilities, B. M. Knepp et al., CRC Critical Review and Therapeutic Drug Carrier Systems, Vol. 4, Issue 1 (1987).

Therefore, transdermal administration is only available for those few active substances, which have an appropriate combination of many favourable characteristics. However, these required characteristics, which should ensure reliable and effective transdermal administration, cannot be predicted for a specific active substance.

The demands to be made on an active substance to make it suitable for transdermal administration are as follows:

Ability to pass through the skin,
No impairment of the adhesive power of the plaster by the active substance,
Avoidance of skin irritations,
Avoidance of allergic reactions,
Favourable pharmacokinetic properties,
Favourable pharmacodynamic properties,
A relatively wide therapeutic window,
Metabolism properties, which are consistent with therapeutic application with continuous administration.

Certainly, the above list of requirements is not exhaustive. The "correct" combination of all these requirements is desirable if an active substance is to be suitable for transdermal administration.

The above specifications in respect of the active substances similarly apply to the composition of the TTS, which contains the respective active substance, and its structure.

Normally, transdermal therapeutic systems (TTSs) involve plasters, which are provided with an impermeable covering layer, a removable protective layer and a matrix containing the active substance or a reservoir containing the active substance with a semipermeable membrane. In the first case, they are known as matrix plasters, in the second case as membrane systems.

For the covering layer, polyester, polypropylene, polyethylene, polyurethane etc. are usually used, which can also be metallized or pigmented. For the removable protective layer, polyester, polypropylene or even paper with a silicon and/or polyethylene coating can also be considered among other things.

Materials based on polyacrylate, silicon, polyisobutylene, butyl rubber, styrene/butadiene copolymer or styrene/isoprene copolymer, are used for the standard pharmaceutical or medical matrices containing the active substances.

The membranes used in membrane systems can be microporous or semipermeable and are usually formed on a basis of an inert polymer, in particular polypropylene, polyvinyl acetate or silicon.

Whilst the matrix structures containing the active substance can be self-adhesive, matrices containing active substance are also produced, depending on the active substance used, which are not self-adhesive, so that the plaster or TTS must consequently be designed with an overtape.

For ensuring the required flux rate of the active substance, skin-penetration enhancers, such as aliphatic, cycloaliphatic and/or aromatic-aliphatic alcohols, in each case monohydric or polyhydric and each including up to 8 C-atoms, an alcohol/water mixture, a saturated and/or unsaturated fatty alcohol each having 8 to 18 carbon atoms, a saturated and/or unsaturated fatty acid each having 8 to 18 carbon atoms and/or its esters as well as vitamins are often necessary as additives.

Furthermore, stabilizers, such as polyvinyl pyrrolidone, α-tocopherol succinate, propyl gallate, methionine, cysteine and/or cysteine-hydrochloride, are frequently added to the matrix containing the active substance.

As the above list shows, numerous TTS constructions and the materials used for these are known. Of course many interacting prerequisites are to be taken into account if a medicament in the form of a TTS should satisfy the medical needs.

The following problems are to be considered when developing TTSs containing active substances:

1. A high loading of the polymer matrix with the active substance is usually necessary to achieve the therapeutically necessary rates of penetration of the active substance through the skin. Active substance remaining in the TTS after administration is complete is therapeutically unused and is disposed of with the plaster. However, for environmental reasons and for reasons of cost, this is undesirable with highly effective and expensive active substances.

2. The polymer matrix, laden with active substance and if necessary also with skin-penetration enhancers, is not physically stable when stored for long periods of time. In particular, a crystallisation of the active substance may occur, which leads to an uncontrollable reduction in the TTS's capacity to release the active substance.
3. A high loading of the polymeric carrier material with active substance and/or skin-penetration enhancers hinders the standardization of the optimum adhesive properties of the transdermal system in the case of self-adhesive polymer films.
4. With applications over several days, the resorption rate of the active substance drops in an unacceptable way, so that additional control layers and/or control constituents are necessary.
5. Should layers, laden with active substance, be made of organic solutions, the problem arises of solvent residues remaining in the layer containing the active substance after the drying process. In addition, there is the risk of an undesirable evaporation of volatile auxiliary agents during manufacture. Since, for reasons of physical stability and skin compatibility of the system, complete freedom from solvent is generally desirable, the reservoir must if necessary be built up in several layers. This again leads to an increase in production costs.

Therefore, the problems as specified above call for a large number of different types of transdermal therapeutic system, these being reflected in the prior art in this field.

For example U.S. Pat. No. 5,662,926 (Wick et al., 1997) gives a more recent overview in this connection. This document describes transdermal systems, which contain a monolithic, thermoplastic polymer film, in which an active substance, preferably nicotine, is homogeneously distributed, as well as a method for the solvent-free manufacture of this layer containing the active substance by mixing the active ingredient with the polymeric carrier material in the polymeric melt at temperatures of 170° C. to 200° C. An additional contact-adhesive film, which is applied on to the matrix containing the active substance, and, if necessary, also a plaster, which is larger in area and is affixed to the polymer film containing the active substance on the side of the matrix turned away from the skin, serves to fix the matrix film containing the active substance on to the skin.

Similar design principles for transdermal systems or plasters containing active substances are also described in PCT/US96/09692 and DE 196 26 621 in respect of plaster preparations containing pergolide. According to both documents, the skin penetration of pergolide from the polymer matrices can be increased by special penetration enhancers. In PCT/US96/09692, the ethylene vinyl acetate (EVA) copolymers used as active-substance carriers for the incorporation of pergolide are dissolved in a suitable organic solvent. In DE 196 26 621, pergolide is incorporated in the acrylate polymers used as active-substance carriers, by dispersing the active substance in a solution of polymers in organic solvents. Films are then produced in each case by forming layers and removing the organic solvent from the corresponding mixture of polymer/active substance/penetration enhancer.

According to PCT/US96/09692, for the treatment of Parkinson's Disease, pergolide-plasma levels in the order of 0.1–1 ng/ml are to be strived for, corresponding to a release rate of at least 100 $\mu$g/h, preferably 150 $\mu$g/h.

In the development of transdermal systems, polymers based on acrylic acid esters and methacrylic acid esters are of particular interest on account of their relatively good absorbency and delivery capability in respect of a multitude of active substances. In order to avoid the use of solvents when manufacturing matrix systems on a poly(meth)acrylate basis, DE 4310012 describes a dermal therapeutic system, in which one or more layers made of mixtures of poly(meth)acrylates are built up and produced from the melt and the first constituent of the mixture consists of (meth)acrylic polymers, which contain functional groups, the second constituent of the mixture regulates the flow properties and only contains insignificant quantities of functional groups. The systems made of poly(meth)acrylates with functional groups should facilitate a controlled delivery of the active substance(s) to or through the skin and a simple method of manufacture. However, experience shows that, with such systems, the advantages regarding manufacture when compared with solvent-based methods are counterbalanced by a number of disadvantages caused by the following:

1. More prolonged thermal loading of all TTS constituents during (1) preparation of the polymeric melt, (2) homogeneous incorporation of the active substance(s) and/or (3) coating of the hot mass containing the active substance(s) on to suitable carrier materials with increased risk of decomposition or disintegration reactions in the polymeric melt and/or during storage of the polymer films containing the active substance(s).
2. Difficulties in optimising the co-/adhesion balance of the layer containing poly(meth)acrylate, since a crosslinking of the acrylate copolymer by means of covalent bonds during manufacture of the polymer matrix containing the active substance in the melt is not possible, combined with problems, which can arise due to a cold flow of the polymeric mass when applying to the skin and/or during storage.

As the above list shows, many designs of plaster and materials used for these are known. Nevertheless to date, in respect of many active substances processed to form transdermal therapeutic systems, there is a great need to provide TTSs, which facilitate the therapeutic delivery of active substances without involving an expensive construction, and which produce an optimum relationship in the overall aspect of their component parts. This also applies to the active substance pergolide if it is to be administered transcutaneously.

Pergolide is therapeutically used alone or in combination with other active substances for the treatment of Parkinson's Disease. The transcutaneous administration of pergolide by means of a TTS is desirable since, by bypassing the gastrointestinal tract and the first passage through the liver, concentration peaks of pergolide in the blood, which can lead to the occurrence of undesirable effects, such as hallucinations, dizziness, nausea and vomiting, are avoided. By bypassing the hepatic first-pass metabolism, the bioavailability of pergolide can be increased compared with oral administration, and the total dose necessary for achieving the therapeutically desired effect can be reduced.

The objective of the present invention is therefore to avoid the above disadvantages of TTSs with pergolide and to provide a structurally simple, skin-compatible TTS, which is physically and chemically stable over a longer storage period and a longer period of application, for the transcutaneous administration of pergolide and which, a) with a low loading of active substance per unit of area, releases as much active substance as possible to and through the skin, b) when administration is complete, has as far as possible delivered all the contained active substance to the skin, and c) is free of solvent.

To achieve this objective, a TTS and a method for its manufacture without using solvents is provided, its special composition surprisingly satisfying the above criteria. It includes a matrix mass containing pergolide and taking the form of a layer, the matrix mass containing a (meth)acrylate copolymer containing ammonio groups or a mixture of a (meth)acrylate copolymer containing amino groups and a (meth)acrylate polymer containing carboxyl groups, 10 to 50% by weight propylene glycol and up to 5.0% by weight pergolide or a pharmaceutically acceptable salt thereof (calculated as a base) and this is surrounded, apart from its release area at the point of application, by a larger plaster, which is free of active substance, for fixing to the skin.

In the sense of the invention, the following terms and/or words have the following meanings:

a) "free of solvent": for manufacturing polymer matrices, no solvents are used, which are largely removed again in the course of the manufacturing process, as occurs in the so-called "solvent based" method.

b) "several days": the TTS can be applied to the skin for therapeutic application for a period of from 1 up to 3 days.

c) "solid solution": the pharmaceutically active substance is distributed in the plaster matrix so as to be molecularly dispersed On the basis of the composition according to the invention and the structural design of the TTS, it is surprising that high proportions of propylene glycol can be stably incorporated in the polymer matrix without the propylene glycol bleeding out from the plaster matrix during long-term storage.

According to a preferred embodiment, 0.5 to 2% by weight pergolide or a pharmaceutically acceptable salt thereof (calculated as a base) is contained in the polymer matrix.

Pergolide can be contained in the TTS as a free base or in the form of one of its pharmaceutically acceptable acid addition salts, such as for example pergolide hydrochloride, acetate or mesylate, in the polymer matrix. Preferably pergolide mesylate is contained in the polymer matrix.

According to another embodiment, the matrix mass containing pergolide contains one or more lipophilic skin-penetration enhancers and/or one or more softening agents.

Suitable skin-penetration enhancers are for example saturated and/or unsaturated fatty acids each having 8 to 18 carbon atoms, their esters with monohydric or polyhydric aliphatic alcohols or saturated and/or unsaturated fatty alcohols each having 8 to 18 carbon atoms.

Propylene glycol monolaurate is preferably contained as skin-penetration enhancer in the matrix mass containing the pergolide.

Suitable softening agents are for example triesters of citric acid with alkanols each having 1–4 carbon atoms, triesters of glycerol with alkane acids each having 1–4 carbon atoms, diesters of phthalic acid with alkanols each having 1–4 carbons atoms and polyoxyethylene-polyoxypropylene copolymers having a molecular mass between 5,000 and 10,000.

Preferably contained softening agents are citric acid tributyl esters and/or citric acid triethyl esters.

According to a further embodiment of the invention, the carrier foil of the TTS has a metal-vapour or oxide coating on the matrix side.

The TTS according to the invention can be manufactured according to the method described below.

A coatable matrix mass containing pergolide is produced by melt extrusion, a coat of homogeneous polymeric melt, at a temperature of up to 150° C. and consisting of a (meth) acrylate copolymer containing ammonio groups or a mixture of a (meth)acrylate copolymer containing amino groups and a (meth)acrylate polymer containing carboxyl groups, 10 to 50% by weight propylene glycol, up to 5.0% by weight pergolide or a pharmaceutically acceptable salt thereof (calculated as a pergolide base) as well as possibly one or more skin-penetration enhancers and/or one or more softening agents, is continuously applied to a thickness of 0.02–0.4 mm on to a carrier, the produced 2-layer laminate is provided with a covering layer and a larger plaster, free of active substance, is applied on to this for fixing the TTS to the skin.

The essential advantage of the method according to the invention compared with the so-called "batch method" lies in that (I) the polymer matrix containing the active substance is manufactured without the use of organic solvents, and (II) the matrix mass containing the active substance is prepared and further processed to form a layer containing the active substance in one continuous and economical operation: process times can be shortened to a few minutes. Consequently, the risk of decomposition reactions in the polymeric melt containing the active substance can be excluded to that extent.

Also, due to the continuous production of the polymeric mass containing pergolide, scaling-up problems are avoided, i.e. when increasing the quantity of the charge or mixture for manufacturing the polymeric melt, containing the active substance, and the laminate, it is not necessary to change to a larger production plant, which usually involves time-consuming and expensive installation, qualification and validation work as well as possibly also formula changes.

BRIEF DESCRIPTION OF THE DRAWING

The structure of the TTS according to the invention is represented in FIG. 1.

It consists of a polymer matrix (1) containing the active substance, a detachable protective foil (5), an inner covering foil (2) and also an overtape, consisting of carrier foil (4) and adhesive film (3).

Figure 1:
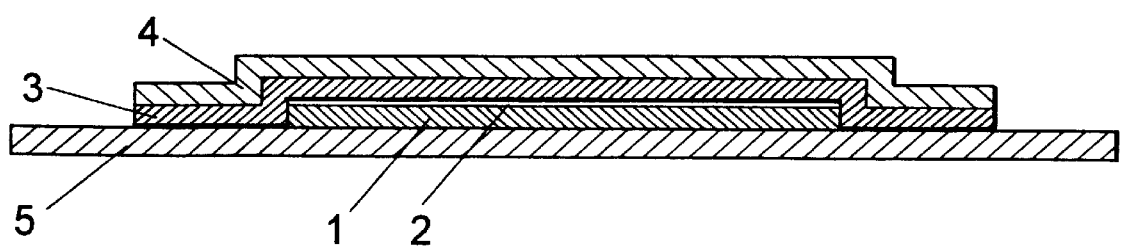

The invention is described with reference to the following examples:

EXAMPLES 1 to 4

A twin screw extruder running in the same direction and equipped with 2 dosing devices is continuously charged in two successive operational zones with a solid constituent or homogeneous mixture of solids (constituent A) as well as a liquid constituent B (for the composition of constituents A and B, see Table 1). The mixture is melt-extruded with a total throughput of 1 kg/h at a temperature of 140° C., the constituent A being continuously weighed in from dosing device 1 in the first operational section and the constituent or solution B being continuously weighed in from liquid dosing device 2 in the second operational section (dosing rates, see Table 2). After leaving the extruder, the produced hot polymeric melt containing pergolide is directly applied in a layer on to an approximately 100 µm thick polyester foil (=protective foil (5)) so that the weight of the layer of the polymeric mass amounts to approximately 50 g/m². After cooling, the two-layer laminate, consisting of protective foil and matrix mass, is covered with an approximately 20 µm thick polyester foil (=inner covering foil (2)).

The outlines of matrix pieces, 5 cm² in size, are punched out from the produced strip of three-layer laminate, the inner covering foil (2) and the polymer matrix (1) containing the active substance being cut through but not the protective foil (5). The resulting intermediate portions are screened off. A self-adhesive overtape foil made up of two layers, consisting of a contact adhesive film (3) based on a crosslinked acrylate copolymer and a (an outer) carrier foil (4) made of polyurethane, is bonded on to the produced strip of laminate having TTS matrices punched to size. The resulting laminate is punched out to form plasters 20 cm² in size, consisting of the component parts (1), (2), (3), (4), (5) according to FIG. 1.

TABLE 1

Manufacturing Formula of Examples 1 to 4

| Constituent | Example 1 % by wt. | Example 2 % by wt. | Example 3 % by wt. | Example 4 % by wt. |
|---|---|---|---|---|
| Constituent A (solid) | | | | |
| Pergolide mesilate | 1.67 | 1.74 | 1.47 | ./. |
| Eudragit 4135 F[1] | 13.33 | 13.91 | ./. | 13.56 |
| Eudragit E 100[2] | 85.00 | 84.35 | ./. | 86.44 |
| Eudragit RS 100[3] | ./. | ./. | 98.53 | ./. |
| Constituent B (liquid) | | | | |
| Propylene glycol (PG) | 100.00 | 94.12 | 100.00 | ./. |
| Propylene glycol monolaurate | ./. | 5.88 | ./. | ./. |
| 2.5% P-mesilate solution in PG | ./. | ./. | ./. | 100.00 |

1) Copolymer made of methacrylic acid, methylacrylate and methylmethylacrylate; corresponds to the polymer constituent of the aqueous dispersion Eudragit 4110 D in accordance with Technical Code of Practice Preparation Eudragit 4110 D, 05/97, Messrs Röhm, Darmstadt, Germany
2) Copolymer made of dimethylaminoethylmethylacrylate and neutral methacrylic acid esters with formic and butyric acid; corresponds to Standard Sheet Eudragit 100, 01/96, Messrs Röhm, Darmstadt, Germany
3) Copolymer made of acrylic and methacrylic acid esters, corresponding to "Ammino Methacrylate Copolymer" Type B according to USP 23/NF 18

TABLE 2

Manufacturing Parameters (Dosing Rates) for Examples 1 to 4

| | Dosing Rate g/h | | | |
|---|---|---|---|---|
| | Example 1 | Example 2 | Example 3 | Example 4 |
| Solid dose (Constituent A) | 600 | 575 | 680 | 1,180 |
| Solid dose (Constituent B) | 400 | 425 | 320 | 820 |

Flux Measurements of the Pergolide in Vitro
a) Flux Measurements through Mouse Skin A TTS matrix with a punched-out area of 2.5 cm² is fixed in a horizontal diffusion cell on the horny layer side of the skin of the stomach and back of hairless mice. Immediately afterwards, the acceptor chamber of the cell is filled, free of air-bubbles, with phosphate buffer solution, pH 6.2 (Ph. Eur., pH 6.4 R; adjusted with phosphoric acid to pH 6.2), which has previously been brought to the temperature of 32° C., and the releasing medium is temperature-regulated to 32±0.5° C.

When taking the samples (after 3; 6; 24; 30; 48; 54 and 72 hours), the releasing medium is exchanged for fresh medium, temperature-regulated to 32±0.5° C.

The amount of pergolide mesilate in the releasing medium or acceptor medium is determined by means of high-pressure liquid chromatography under the conditions specified below. Stationary phase: Supelcosil LC-8-DB, 75 mm×4.6 mm, 3 μm; 45° C.; column temperature: 40° C.; eluent: 550 parts by volume water, 450 parts by volume methanol and 1.7 parts by volume dibutyl amine, adjusted to pH 3.0 with phosphoric acid; detection: fluorescence, excitation wavelength=280 nm, emission wavelength=346 nm; flow rate: 1.5 ml/min.; injection volume: 25 b) Flux Measurements through Human Skin

A sample of skin stored for a maximum of 8 weeks at −18° C. from the abdominal area of a woman was used. The pieces of skin used for the flux measurements were prepared by separating the dermis by means of heat separation (Klingman & Christopher, 88, Arch. Dermatol. 702 (1963)) in water heated to 60° C., the obtained epidermal membrane was stored on filter paper at −18° C. for a maximum of 1 week and thawed overnight prior to carrying out the measurement.

The TTS matrix was fixed in a modified Franz cell with a releasing or diffusion area of 1 cm² on the horny layer side of the excised skin preparation. Immediately afterwards, the acceptor chamber of the cell (2.3 cm³ volume) was filled, free of air-bubbles, with phosphate buffer solution pH 6.2 (Ph. Eur., pH 6.4 R; adjusted with phosphoric acid to pH 6.2) and the releasing medium was temperature-regulated to 37±0.5° C. (in accordance with a skin surface temperature in the used diffusion cell of 32° C.).

At the times samples were taken (after 3; 6; 9; 12; 24; 36; 48 hours), the releasing medium was exchanged for fresh, temperature-regulated medium.

The amount of pergolide mesilate in the releasing or acceptor medium is determined by means of high-pressure liquid chromatography under the conditions specified below. Stationary phase: Supelcosil LC-8-DB, 150 mm×4.3 mm, 3 μm; 45° C.; column temperature: 40° C.; eluent: 55 parts by volume water, 45 parts by volume methanol and 1.7 parts by volume dibutyl amine, adjusted to pH 3.0 with phosphoric acid; detection UV at 280 nm; flow rate: 1.0 ml/min.; injection volume: 20 μl.

The results of the investigations in respect of test samples according to Examples 1 to 3 are summarized in Table 3. Table 4 contains a summary of the flux rates of polymer matrix systems or solutions known from the prior art according to PCT/US96/09692, which have a percentage by mass of pergolide of 5–10% by weight and 2 and 5% by weight respectively.

A comparison of the flux rates shows that the TTS according to the invention releases pergolide in surprisingly high rates through the skin, despite having a percentage by mass of less than 1% by weight and thus a clearly reduced loading with the active substance when compared with the comparative examples. Thus, the matrix according to Example 2 contained in the TTS according to the invention, which contains a percentage of active substance of only 0.87% by weight, with 2.4 μg/cm²/h even has a higher flux through human skin than all the matrix formulations of PCT/US96/09692, which contain a percentage of pergolide of up to 10% by weight as well as high percentages of skin-penetration enhancers. This result is all the more surprising because the flux measurement was carried out with an acceptor medium warmed to 32° C., i.e. at a temperature 3° C. lower than in PCT/US96/09692, thus under conditions, which are clearly less favourable in respect of penetration of the active substances.

Moreover, it emerges that the quantity of pergolide contained in the TTS according to the invention can be released practically quantitatively through the skin in the experimental period of 2 days. This is particularly advantageous since, after administration is complete, residual quantities of the highly effective and expensive active substance remaining in the TTS can thus be avoided.

TABLE 3

Pergolide Flux Rates through Excised Skin Preparations (Examples 1–3)

| Preparation | Amount of pergolide mesilate in the matrix % by wt. (mg/16 cm²) | Flux Rate (µg/cm²/h) | Average cumulative flux rate (µg/12 cm²) | |
|---|---|---|---|---|
| | | | After 24 h | After 48 h |
| Mouse skin | | | | |
| Example 1: | 0.61% (0.48 mg ± 10%) | 1.0 | 394 (82%)* | 454 (95%)* |
| Example 2: | 0.87% (0.78 mg ± 10%) | 1.8 | 687 (88%)* | 815 (ca. 100%)* |
| n = 3 | | | | |
| Human skin | | | | |
| Example 1: | 0.61% (0.48 mg ± 10%) | 1.0 | 258 (54%)* | 302 (63%)* |
| Example 2: | 0.87% (0.78 mg ± 10%) | 2.4 | 576 (74%)* | 682 (87%)* |
| n = 4 | | | | |
| Mouse skin | | | | |
| Example 3: | 0.67% (0.71 mg ± 10%) | 1.5 | 559 (79%)* | 609 (86%)* |
| n = 3 | | | | |

*) = cumulative flux in % by weight relative to the actual specified amount of active substance in the matrix.

TABLE 4

Pergolide Flux Rates through Excised Skin Preparations (PCT/US96/09692)

| Preparation | Content of pergolide mesilate in matrix or donor % by wt. | Flux rate* µg/cm²/h |
|---|---|---|
| (1) P.-mesilate solution in H₂O | 2 | ca. 1.1 |
| (2) P.-mesilate solution in H₂O/ethanol | 5 | ca. 2–4 |
| (3) P.-mesilate in EVA polymer matrix | 5–10 | 0.5–2.2 |

*) = Tests with excised human skin; 35° C.

What is claimed is:

1. A transdermal therapeutic system for a transcutaneous administration of pergolide over several days with a means of fixing the system onto skin, wherein the system comprises a matrix mass comprising pergolide and taking a form of a layer, which contains a copolymer consisting essentially of (a) a (meth)acrylate copolymer containing ammonio groups or (b) a mixture of a (meth)acrylate copolymer containing amino groups and a (meth)acrylate polymer containing carboxyl groups, 10 to 50% by weight propylene glycol, and 0.5% to less than 5.0% by weight pergolide or a pharmaceutically acceptable salt thereof calculated as a base, said matrix, with the exception of a releasing area at the point of application, is surrounded by a larger plaster for fixing the matrix to the skin, said plaster being free of pergolide.

2. The system according to claim 1, wherein the matrix mass contains 0.5 to 2% by weight of pergolide or a pharmaceutically acceptable salt thereof, calculated as a base.

3. The system according to claim 1 wherein the matrix mass contains pergolide mesylate.

4. The system according to claim 1 wherein the matrix mass contains one or more lipophilic skin-penetration enhancers, one or more softening agent, or both.

5. The system according to claim 4 wherein the matrix mass contains propylene glycol monolaurate as the skin-penetration enhancer.

6. The system according to claim 4 wherein the matrix mass contains citric acid triethyl esters, citric acid tributyl esters, or both, as softening agents.

7. The system according to claim 1 wherein the system further comprises a carrier foil having a metal vapor coating or an oxide coating on a surface that contacts the matrix.

8. A method of manufacturing a transdermal therapeutic system of claim 1, wherein a homogeneous polymeric melt, having a temperature of up to 150° C. and comprising a copolymer consisting essentially of (a) a (meth)acrylate copolymer containing ammonio groups or (b) a mixture of a (meth)acrylate copolymer containing amino groups and a (meth)acrylate polymer containing carboxyl groups, 10 to 50% by weight propylene glycol, and 0.5% to less than 5.0% by weight pergolide or a pharmaceutically acceptable salt thereof calculated as a pergolide base, and optionally one or more skin-penetration enhancers, one or more softening agents, or both, is continuously applied in a layer to a thickness of 0.02–0.4 mm on a carrier, the obtained 2-layer laminate is provided with a covering layer, and a larger plaster, which is free of pergolide, is applied onto the covering layer for the purpose of fixing the system to skin.

* * * * *